United States Patent [19]

Cama et al.

[11] 4,218,459
[45] Aug. 19, 1980

[54] 6-AMIDO-1-CARBA-2-PENEM-3-CARBOXYLIC ACID

[75] Inventors: Lovji D. Cama; Burton G. Christensen, both of Metuchen; Ravindra N. Guthikonda, Edison, all of N.J.

[73] Assignee: Merck & Co., Inc., Rahway, N.J.

[21] Appl. No.: 865,169

[22] Filed: Dec. 28, 1977

[51] Int. Cl.² ............... C07D 487/04; A61K 31/40
[52] U.S. Cl. .................. 424/270; 260/239 A; 260/245.2 R; 424/251; 424/263; 424/269; 424/272; 424/273 P; 424/273 N; 424/274; 544/90; 544/333; 546/272
[58] Field of Search ............. 260/326.31, 245.2 T, 260/306.8 R; 424/274, 270

[56] References Cited

U.S. PATENT DOCUMENTS 4,011,216   3/1977   Menard et al. ............... 260/326.31

*Primary Examiner*—Mary C. Lee

*Attorney, Agent, or Firm*—Hesna J. Pfeiffer; Julian S. Levitt; James A. Arno

[57] ABSTRACT

Disclosed are 6-amido-1-carba-2-penem-3-carboxylic acids of the following structure:

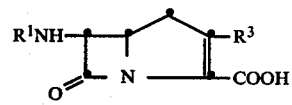

wherein $R^1$ is hydrogen or acyl and $R^3$ is, inter alia, independently selected from the group consisting of hydrogen, alkyl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

15 Claims, No Drawings

6-AMIDO-1-CARBA-2-PENEM-3-CARBOXYLIC ACID

BACKGROUND OF THE INVENTION

This invention relates to 6-amido-1-carba-2-penem-3-carboxylic acids and their pharmaceutically acceptable salt and ester derivatives, which compounds are useful as antibiotics and which may be represented by the following generic structural formula (I):

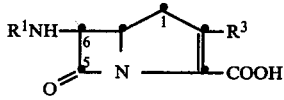

wherein $R^1$ is hydrogen or an acyl radical conventionally known in the related, bicyclic β-lactam antibiotic art, such as the penicillins and cephalosporins; and $R^3$ is selected from the group consisting of hydrogen, substituted and unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl and heterocyclylalkyl wherein the substituent or substituents relative to the above named radicals are selected from the group consisting of amino, hydroxy, alkoxyl, mercapto, alkylthio, arylthio, sulfamoyl, amidino, guanidino, nitro, chloro, bromo, fluoro, cyano and carboxy; and wherein the hetero atom in the above-named heterocyclic moiety is selected from the group consisting of oxygen, nitrogen and sulphur.

This invention also relates to the pharmaceutically acceptable salt, ester and amide derivatives of the compounds of the present invention identified by structure I, above.

This invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus, Strep. pyogenes* and *B. subtilis*, and gram negative bacteria such as *E. coli*, Pseudomonas, *Proteus morganii*, Serratia and Klebisiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

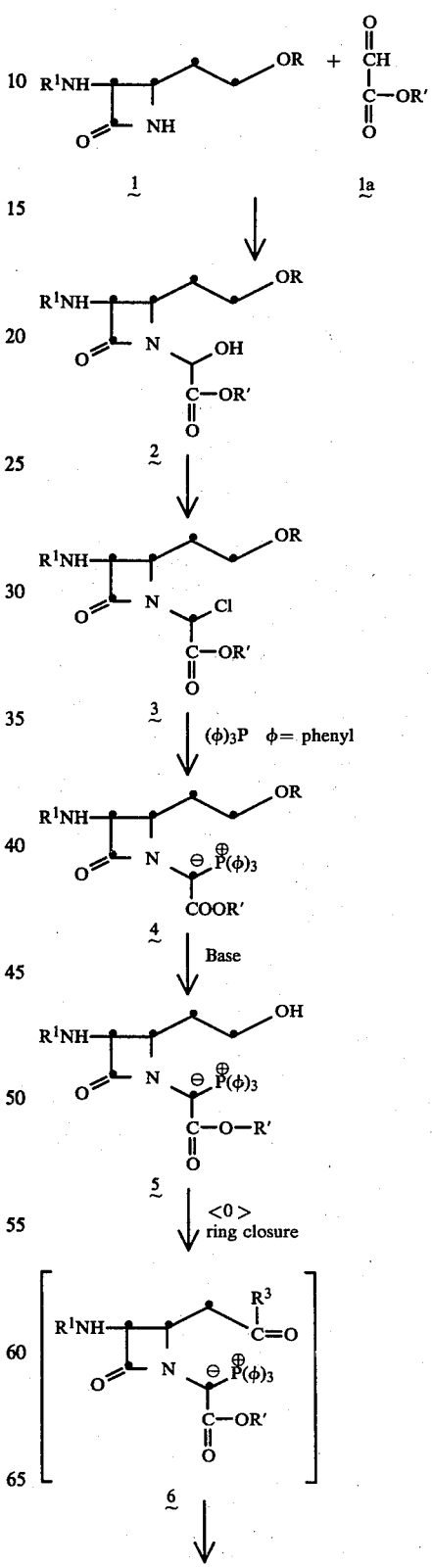

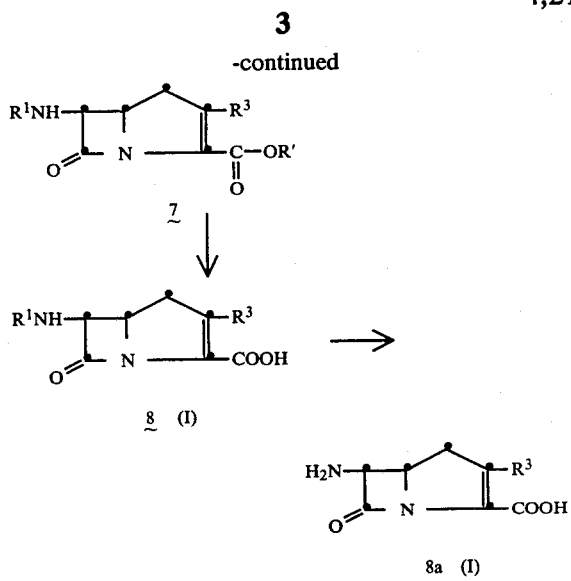

wherein R¹, and R³ are as defined; and R and R' are readily removable blocking groups; R' may also be a pharmaceutically acceptable ester moiety. Typically, the blocking group R is an acyl such as a lower alkanoyl, aralkylcarbonyl or the like such as acetyl, bromo-t-butoxycarbonyl, benzyloxycarbonyl, formyl, trifluoroacetyl and the like or a trialkylsilyl such as trimethylsilyl or t-butyl dimethylsilyl group; and typically the blocking group R' is substituted or unsubstituted alkyl, aralkyl, alkenyl, or the like such as benzyl, p-nitrobenzyl, o-nitrobenzyl, pivaloyloxymethyl, bromo-t-butyl and the like.

In words relative to the above reaction diagram, a suitably substituted azetidinone (1) is reacted with a glyoxalate ester such as benzyl glyoxalate to form the corresponding 1-(benzyloxycarbonylhydroxymethyl) azetidinone (2). The reaction 1→2 is conveniently carried out in a solvent such as benzene, toluene, xylene and the like at a temperature of from about 25° C. to reflux for from 2 to 10 hours. There is no criticality as to the precise identity of the solvent, provided only that it adequately solubilizes the reactants and be inert or substantially inert to the desired course of reaction. The halogenation reaction 2→3 may be conducted by any of a variety of well-known halogenation means. Suitable reagents include: SOCl₂, POCl₃, oxalyl chloride and the like. A preferred means of chlorination involves treating 2 in a solvent such as tetrahydrofuran (THF), ether, CH₂Cl₂ and the like with thionylchloride in the presence of 1 to 2 equivalents (relative to the thionylchloride) of a base such as pyridine, triethylamine, quinoline and the like. Typically, the reaction is conducted at a temperature of from −30° to 25° C. for from 0.5 to 1 hour. The resulting 1-(benzyloxycarbonylchloromethyl)-azetidinone species, 3, is isolated, if desired, by conventional procedures for later reaction, 3→4. The intermediate 4 is prepared from 3 by treating 3 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2cyanoethyl)phosphine or the like. Typically the reaction is conducted under a nitrogen atmosphere at a temperature of from −20° to 25° C., for from 0.5 to 2 hours. The reaction 4→5 may be achieved by any of a variety of well-known deblocking procedures such as hydrolysis or hydrogenolysis. A particularly convenient means for the deblocking, 4→5, is by an alcoholysis procedure comprising treating 4 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours. The preparation of intermediate 6 from 5 with establishment of R³ is described below. The ring closure reaction 5→7 proceeds via the oxo intermediate 6 and is achieved by treating 5 with an equivalent of an oxidizing system such as 1:1 mixture of dimethylsulfoxide (DMSO) and acetic anhydride (Ac₂O); other oxidizing system includecyclohexylcarbodiimide in DMSO, pyridinium chlorochromate, and CrO₃.2 (pyridine) in CH₂Cl₂, for example. Typically, the closure step 5→7 is conducted at a temperature of from about 0° to 100° C. for from 0.25 to 24 hours in the oxidative system (DMSO/Ac₂O) described above or by heating from 100°–160° C. (after isolation of the oxo compound 6) in a solvent such as benzene, toluene, dioxane, xylene, or DMF. The carboxyl deblocking step 7→8, where R' is a pharmaceutically effective acyl, may be achieved by a number of well-known procedures such as hydrolysis, hydrogenation, or photolysis of a suitable R' group. Suitable hydrogenation catalysts for deblocking include the platinum metals and their oxides such as palladium on carbon and the like; suitable solvents for the hydrogenation include methanol, dioxane/H₂O, ethanol/H₂O and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

In the case where R₁ is an N-blocking group rather than a pharmaceutically acceptable acyl radical it is removed by hydrogenation or photolysis. Suitable N-blocking groups include: benzyloxycarbonyl, p-nitrobenzyloxycarbonyl, o-nitrobenzyloxycarbonyl, p-methoxybenzyloxycarbonyl, 3,5-dimethoxybenzyloxycarbonyl and the like. Suitable hydrogenation catalysts are platinum metal and their oxides such as palladium on carbon and the like. Suitable solvent for the hydrogenation include methanol, dioxane/water ethanol/water and the like, in the presence of hydrogen at a pressure of from 1 to 50 atmospheres; the hydrogenation is typically conducted from 5 minutes to 4 hours at a temperature of about 25° C. Alternatively if R¹ is a photolabile protecting group it can be removed by photolysis in a pyrex vessel using light of wave length of 350 nm in a solvent such as dioxane/H₂O, THF/H₂O EtOH/H₂O or the like. The photolysis is typically conducted from 5 min. to 4 hours at a temperature from 0° to 25°. Both hydrogenation or photolysis may be conducted in the optional presence of a weak base such as sodium bicarbonate or the like. Usually R¹ and the carboxyl protecting group R' are chosen such that both may be removed simultaneously but optionally they may be removed consecutively.

The amino acid 8a (the 6-amino species) can be acylated by conventional acylating methods using an acid chloride, acid anhydride, or mixed anhydride in the presence of a mild base in a solvent such as acetone water, dioxane/water, THF/water or the like; at a temperature from −10° to 25°. The mild base used may be sodium bicarbonate, triethylamine, pyridine or the like Usually the reaction is carried out from 5 min. to 2 hours.

The glyoxalate esters 1a used to react with 1 can be prepared by oxidation of the corresponding tartaric acid diesters with oxidants such as periodic acid or lead tetraacetate in a solvent such as THF, benzene or methylene chloride at −20° to 25° for ½ to 4 hrs. The tartarate esters are prepared from dilithio tartarate or disodio tartarate by reaction with R'X wherein X is chloro, bromo or iodo and R' is as defined above in a solvent such as DMF or DMSO at 25° to 70° C. for from 4 to 48 hrs. As noted above, R' may be a pharmaceutically acceptable ester moiety. Such pharmaceutically acceptable esters and amides, however, may also be prepared from the free acid of I according to the procedure of co-pending U.S. patent application Ser. No. 733,651 filed Oct. 18, 1976, which is directed to the pharmaceutically acceptable esters and amides of thienamycin and their preparation. Accordingly, for its disclosure relative to such pharmaceutically acceptable forms and their means of preparation, the above-cited application is incorporated herein by reference.

The following diagram summarizes the synthesis of the essential starting material, 1.

3 by hydrolysis. The reduction of 3 to provide the 4-(2-acetoxyethyl)-2-azetidinone (4) is conducted by any convenient means such as hydrogenation in the presence of a catalyst such as platinum, palladium or oxides thereof under a hydrogen pressure of from 1 to 20 atmospheres in a solvent such as ethanol, ethylacetate, or the like at a temperature of from 0° to 25° C., for from 5 minutes to 1 hour. The 4-(2-hydroxyethyl)-2-azetidinone species, 5, is obtained from 4 by hydrolysis. The 8-oxo-2,2-dimethyl-3-oxa-1-azabicyclo[4.2.0]octane species, 6, is obtained on treatment of 5 with 2,2-dimethoxypropane in the presence of a catalyst such as boron trifluoride etherate in a solvent such as methylene chloride at a temperature of from 0° to 40° C. for from 1 to 40 minutes. The azide intermediate 7 is prepared by treating 6 in a solvent such as tetrahydrofuran (THF), dimethoxyethane, dioxane, DMF or the like with a base such as lithium diisopropylamide, butyl lithium, phenyl lithium or the like at a temperature of from −25° to −78° C. for from one to three hours; whereupon an azide reagent such as tosylazide is introduced; after 1 to 3 hours at −35° to −50° C. the mixture is treated with a disproportionating agent such as trimethylchlorosilane to provide the azide 7 which may be isolated. The amino intermediate 8 is prepared by reducing 7 in a solvent such as ethylacetate, ethanol, dioxane, methanol or the like in the presence of a hydrogenation catalyst such as Pd on carbon, PtO$_2$, Pd/CaCO$_3$, or the like and hydrogen (4 to 50 atmospheres) for from 12 to 48 hours Preparation of 1

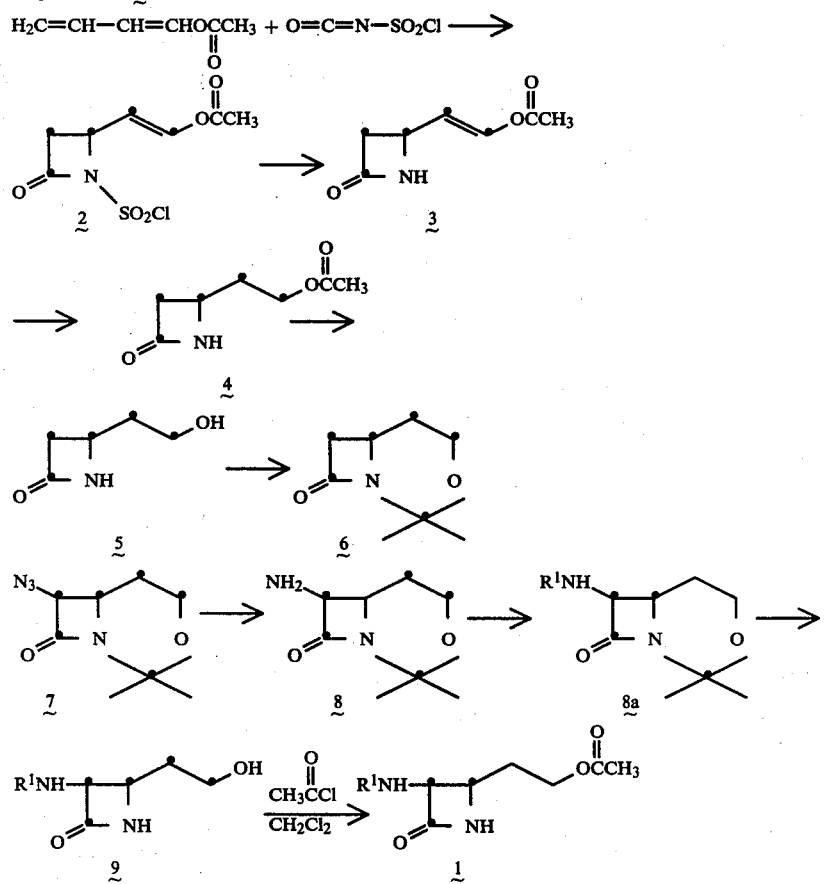

In words relative to the above diagram for the preparation of 1, the 4-(2-acetoxyvinyl)azetidine-2-one (3) is prepared by reacting chloro sulphonyl isocyanate and an acyloxybutadiene such as 1-acetoxybutadiene in a solvent such as anhydrous dimethyl ether at a temperature of from about −30° C. to 0° C. under a nitrogen atmosphere. The reaction intermediate 2 is converted to at a temperature of from 20° to 30° C. The N-acyl intermediate 8a is obtained from 8 on treatment in a solvent such as CH$_2$Cl$_2$, ether, chloroform or the like with the acid chloride of choice calculated to provide the acyl radical R$^1$ at a temperature of from $-25°$ to 0° C. for from 2 to 15 hours. Species 9 is obtained from 8a by acid hydrolysis.

The desired blocked species 1 is obtained by treating 9 with an acylating agent such as acetyl chloride, formic acetic anhydride, trifluoroacetic anhydride and the like in a solvent such as CH$_2$Cl$_2$, CHCl$_3$, THF and the like at a temperature of from $-20°$ to about 25° C. for from 0.5 to about 4 hours. The starting material 1 may be isolated for later reaction in accordance with the procedures of the present invention for the preparation of the compounds of the present invention.

The preferred procedure for establishing the 2-substituent, R$^3$, in the total synthesis of I may be illustrated by the following reaction diagram:

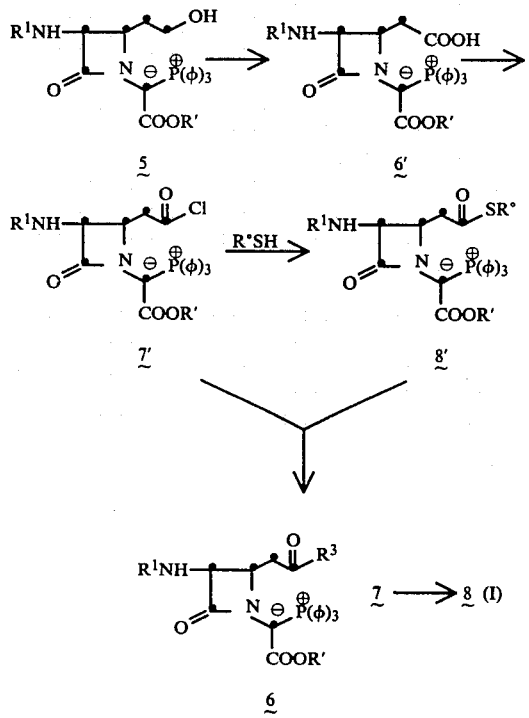

wherein R$^1$, R' and R$^3$ are as defined above, $\phi$ is phenyl and R° is defined below.

In words relative to the above diagram, species 5 is the same as that shown in the first-described reaction diagram. This species, 5, is oxidized to yield 6'. Any of a variety of oxidizing systems may be employed such as Jones' Reagent, KMnO$_4$, Ag$_2$O, and the like in solvents such as acetone, aqueous THF, aqueous dioxane, and the like at a temperature range of from 0° to 25° C. for from 10 min. to 24 hours. The preferred conditions of oxidation, 5→6', comprise treating 5 in a solvent such as acetone, or the like with Jones' Reagent at a temperature of from 0° to 25° C. from 10 min. to 0.5 hours. Chlorination of 6' yields 7'. Typically the chlorination is accomplished by treating 6' in a solvent such as CH$_2$Cl$_2$, THF, Et$_2$O, CHCl$_3$, C$_6$H$_6$, or the like with a chlorinating agent such as oxalyl chloride, SOCl$_2$, POCl$_3$, or the like at a temperature of from $-20°$ to 25° C. for from ½ to 24 hours. Treating 7' with a mercaptan in R°SH such as phenyl mercaptan, butyl mercaptan, ethyl mercaptan, p-nitrophenyl mercaptan or the like in a solvent such as CH$_2$Cl$_2$, Et$_2$O, THF, C$_6$H$_6$, or the like at a temperature of from 0° to 25° C. for from 0.5 to 3 hours provides 8'. In the alternative 7' may be converted directly to 6, then to 7 and 8 (I). Conversion of either 8' or 7' to 6 is accomplished by treating either with (R$^3$)$_2$CuLi or (R$^3$)$_2$CuMgX wherein R$^3$ is as defined above (the ultimate 2-substitutent on species 8, otherwise known as I) in a solvent such as diethylether, tetrahydrofuran, or the like at a temperature of from $-78°$ to 25° C. for from 10 min. to 2 hours. It will be recognized that species 6 (above) is identical to species 6 in the first-defined total reaction scheme and that conversion of 6→7→8 (I) is exactly as described above. In the generic description of the present invention (I, above), the substituent R$^3$ is preferably selected from the group consisting of hydrogen; substituted and unsubstituted: straight and branched loweralkyl having from 1 to 10 carbon atoms; alkenyl, alkynyl, having from 2 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selected from the group consisting of amino, hydroxyl, cyano, carboxyl, nitro, chloro, bromo, fluoro, lower alkoxy having from 1 to 6 carbon atoms, mercapto, perhaloloweralkyl such as trifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

A particularly preferred class of compounds are those wherein R$^3$ is selected from the group consisting of substituted and unsubstituted: loweralkyl having from 1 to 6 carbon atoms, alkenyl having from 2 to 6 carbon atoms, and phenyl; wherein the substituents relative to the above-named preferred radicals are selected from the group consisting of hydroxyl, amino, amidino, guanidino, phenyl, amino alkyl, hydroxy alkyl mercapto, carboxyl, trifluoromethyl, loweralkylthio and loweralkoxyl wherein the alkyl moiety of the loweralkylthio and loweralkoxyl comprises 1 to 6 carbon atoms. In addition, the compounds p(hydroxymethyl)-phenyl, p(aminomethyl)phenyl, p-methoxyphenyl are particularly preferred groups.

The preferred esters used as protecting groups are those where R' is benzyl, p-nitrobenzyl, o-nitrobenzyl, t-butyl, bromo-t-butyl, t-butyl-dimethylsilyl, trimethylsilyl, trichloroethyl; or R' represents pharmaceutically acceptable ester moieties such as pivaloyloxymethyl, allyl, methallyl, (2-methylthio)-ethyl, or 3-buten-1-yl.

In the generic representation of the compounds of the present invention (I, above), the acyl radical represented by R¹ can, inter alia, be substituted or unsubstituted aliphatic, aromatic or heterocyclic, araliphatic or heterocylylaliphatic carboxylic acid radical, a substituted or unsubstituted carbamyl radical or a carbothioic acid radical. One group of acyl radicals can be represented by the general formula:

wherein X is O or S and R″ represents hydrogen; amino; substituted amino such as alkyl- and dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O,N and S; such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R″ is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)-methyl,2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl) methyl, 2-furylmethyl, 2-(5-nitrofuryl)methyl, 3-furylmethyl, 2-theinylmethyl, 3-thienylmethyl, tetrazolylmethyl benzamidinomethyl and cyclohexylamidinomethyl.

The acyl group can also be a radical of the formula:

wherein X is O or S and n is 0–4, Z represents oxygen, sulfur, carbonyl or nitrogen and R″ is defined as above. Representative members of the substituent

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

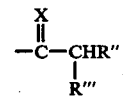

wherein R″ is defined as above and R‴ is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3- or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D-(—)-α-amino-3-chloro-4-hydroxybenzyl, α-amino(-cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxdiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxyl, sulfo, or sulfamino and $R^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1-6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, aminoethyl, nitro, metoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-gaunidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-metoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

$R^1$ of Structure I may also be a readily removable protecting group; a particularly preferred acyl for this purpose is o or p-nitrobenzyloxycarbonyl.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived frm sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried in certain species of I on side chain $R^3$ are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel 6-amido-1-carba-2-penem-3-carboxylic acid of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacterial and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricantors, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product; process, compositional or method of treatment aspects of the present invention. All reaction temperatures are in °C.

EXAMPLE 1

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under $N_2$ for 2-½ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO)δ: 4.8 d (j=7, H—C—OH), 5.23 d (j=7, H—C—OH), 5.7 S (O—CH$_2$—C$_6$H$_4$—NO$_2$); 7.73 & 8.2 m (aromatic H).

Similar treatment of the di-lithium salt with R'X (where X =Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate.

EXAMPLE 2

Preparation of 8-oxo-2,2-dimethyl-3-oxa-1-azabicyclo[4.2.0]octane

Step A

Preparation of 4-(2-acetoxyvinyl)azetidine-2-one

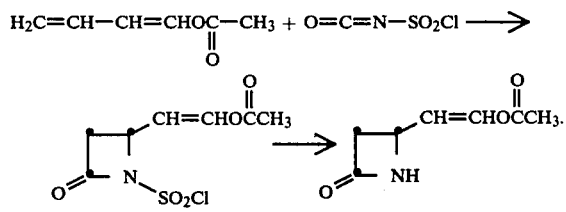

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoxybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6-8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a $N_2$ stream. The product crystallizes from fractions 4-6, with traces in 3 and 7. Fractions 1-3 contain a yellowish sharp-smelling material which resinifies on standing. Yield: 100 mg as a mixture of the cis and trans-isomers.

Step B

Preparation of 4-(2-Acetoxyethyl)-2-Azetidinone

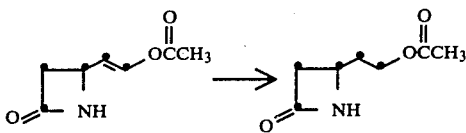

A solution of 4-(2-acetoxyvinyl)-2-azetidinone (10.0 g, 0.065 mole) in 200 ml ethyl acetate containing 100 mg of 10% Pd/C is hydrogenated on a Parr shaker at 25° C. under 40 psig hydrogen for 15 minutes. The mixture is filtered through a bed of Supercel and washed with additional ethyl acetate. The combined filtrate is evaporated in vacuo to give 4-(2-acetoxyethyl)-2-azetidinone (10.0 g) as a crystalline solid. Recrystallization from ether affords white crystals: M.P. 44°-7°; ir $(CHCl_3)_\mu 5.66$, 5.74; nmr $(CDCl_3)\tau 3.44$ (broad s, 1, NH), 5.82 (m, 2, $CH_2OCOCH_3$), 6.29 (m, 1, C-4H), 6.87 (½ AB pattern further split in four by C-4H and NH, 1, $J_{gem}=12.8$ Hz, $J=4.5$ H $J_{NH}=1.9$ Hz, 7.38 (½ AB pattern further split in four by C-4H and NH, 1, $J_{gem}=12.8$ Hz, $J=2.3$ Hz, $J_{NH}=1.0$ Hz), 7.93 and 8.02 (s on m, total 5, $OCOCH_3$ and $CH_2CH_2OCOCH_3$, respectively).

Step C

Preparation of 4-(2-Hydroxyethyl)-2-Azetidinone

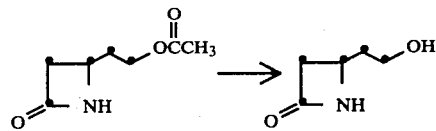

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/$CHCl_3$ to give 1.55 g of the alcohol: m.p. 50°; ir $(CHCl_3)\mu$ 5.67; nmr $(CDCl_3)\tau 3.20$ (broad s, 1, NH), 6.24 and 6.28 (m on t, total 3, C-4H and $CH_2OH$ respectively), 6.90 (broad s on ½ AB pattern further split in four by C-4H and NH, total 2, OH and C-3H respectively, $J_{gem}=13.0$ Hz, $J_{vic}=4.2$ Hz, $J_{NH}=1.6$ Hz), 7.42 (½ AB pattern further split in four by C-4H and NH, 1, C-3H, $J_{gem}=13.0$ Hz, $J_{vic}=2.2$ Hz, $J_{NH}=1.1$ Hz), 8.16 (m, 2, $CH_2CH_2OH$).

Step D

Preparation of 8-Oxo-2,2-dimethyl-3-oxa-1-azabicyclo[4.2.0]octane

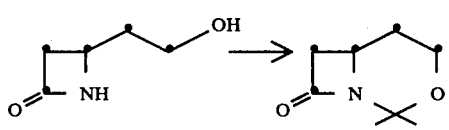

A solution of 4-(2-hydroxyethyl-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes.

Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]octane (1.59 g) as a crystalline solid. Recrystallization from ether/hexane gives product of m.p. 60°–1°.

ir (CHCl$_3$)$\mu$: 5.73 ($\beta$-lactam).
nmr (CDCl$_3$)$\tau$:
6.02–6.28, m, 2 H, C-4 methylene
6.22–6.62, m, 1 H, C-6 methine
6.90, dd, 1 H, $J_{7,7}=14$ Hz, $J_{6,7}=4.5$ Hz C-7 proton cis to C-6H
7.47, dd, 1 H, $J_{7,7}=14$ Hz, $J_{6,7}=2$ Hz C-7 proton trans to C-6H
7.82–8.68, m, 2 H, C-5 methylene 8.23, s, 3H  
8.57, s, 3H  } C-2 methyls

EXAMPLE 3

Preparation of 7-amino-8-oxo-2,2-dimethyl-3-oxa-1-azabicyclo[4.2.0]octane

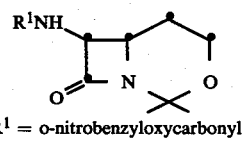

R$^1$ = o-nitrobenzyloxycarbonyl

Step A

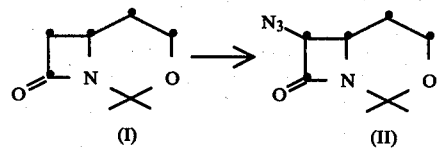

A solution of 1.54 ml (11 mmoles) of diisopropylamine in 30 ml of dry THF is cooled to −78° C. in dry-ice/acetone bath; 6.11 (11 mmoles) of 1.8 M methyllithium is added dropwise under nitrogen. The resulting solution is stirred at the same temperature for 1 hour; 1.55 g (10 mmol) of the bicyclic azetidinone I in 10 ml of dry THF is added dropwise. The mixture is stirred for 1 hr at −78° C. Then, 2.17 g (11 mmoles) of tosylazide in 5 ml of dry THF is added dropwise. The resulting mixture is warmed to −50° C. and kept for 1.5 hours at that temperature; 2.54 ml (20 mmol) of trimethylchlorosilane is added and the mixture is heated at reflux for 6 hrs. The reaction mixture is cooled and the solid is filtered off and washed with 2×25 ml of ether. The filtreate is concentrated. The residue is taken up in 100 ml of water and extracted with 3×25 ml of methylene chloride. The combined extracts are dried over anhydrous MgSO$_4$, concentrated, and the residue is chromatographed on silica gel (eluant 50:50:ethylacetate:cyclohexane) to give the desired azido azeitidinone II as solid (45% yield). IR., $\mu$: 4.66 (azide), 5.61 (⊕-lactam; nmr:$\delta$, 4.21 (C7-H; trans; J=2); 4.75 (C7-H, cis; J=5), 3.4–3.75 m (C6-H, cis and trans); 1.45 and 1.75 (s) (CH$_3$).

Step B.

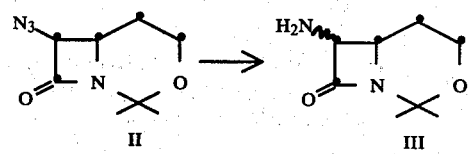

The azetidinone II (1.96 g) is dissolved in 50 ml of ethylacetate and 100 mg of 10% Pd on carbon is suspended. The azide is then shaken in a Parr shaker in an atmosphere of hydrogen at 4.5 psi at 25° C. After 24 hr., the catalyst is filtered off on 'supercel' and the filtrate is concentrated to give the amine III.

Step C

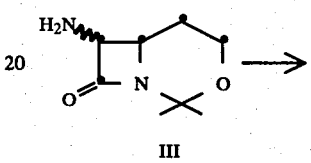

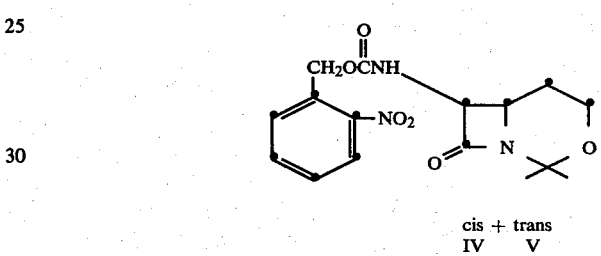

cis + trans
IV    V

The amine resulting from Step B is dissolved in 50 ml of CH$_2$Cl$_2$ and cooled to 0° C. in an ice bath; 800 $\mu$l of pyridine is then added. After 5 minutes, 2.155 g of o-nitrobenzyloxycarbonyl chloride is added dropwise. The reaction mixture is warmed to 25° C. over a period of 1 hr. and washed with 2×25 ml of water. The organic phase is dried over MgSO$_4$, and concentrated to give a gum, which is chromatographed on silica gel, eluting with ethylacetate/cyclohexane mixture to separate the cis and trans isomers IV and V, respectively.

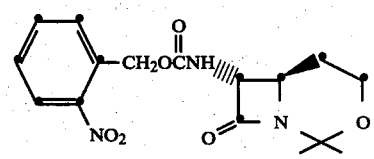

nmr; (CDCl$_3$/D$_6$-DMSO); $\delta$; 7.47–8.4 (aromatic); 5.43 S (benzyl CH$_2$); 4.33 dd (J=2, J=8); (C7-H, trans); 1.39 & 1.61 S (CH$_3$).

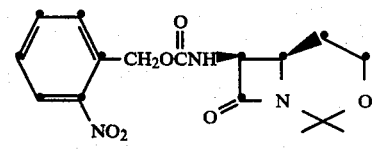

nmr; (CDCl$_3$/D$_6$-DMSO); $\delta$; 7.4–8.3 (aromatic); 5.43 S (benzyl CH$_2$); 4.9 dd (J=4.5; J=8); C 7-H; cis; 1.4 & 1.65 S (CH$_3$).

EXAMPLE 4

Preparation of 1-(o-nitrobenzyloxycarbonylmethylenetriphenylphosphoranyl)-3-(o-nitrobenzyloxycarbonylamino)-4-(2-hydroxyethyl)-2-azetidinone

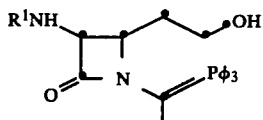

R¹ = o-nitrobenzyloxycarbonyl
R' = o-nitrobenzyl
φ = phenyl

Step A

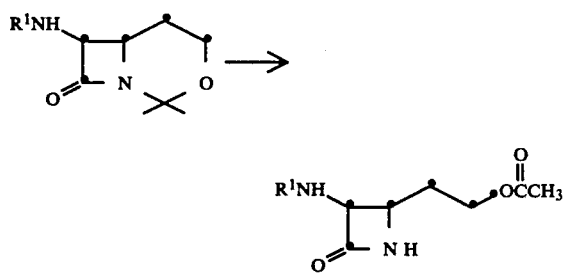

A quantity (3.49 g) of trans-7-[o-nitrobenzyloxycarbonylamino]-8-oxo-2,2-dimethyl-3-oxa-1-azabicyclo[4.2.0]octane is dissolved in 10 ml of 2:1 mixture of trifluoroacetic acid and water. After standing at 25° C. for 10 min. most of the solvent is removed in vacuo at 25°. The residue is taken up in 50 ml of benzene and evaporated to dryness in vacuo at 25°. The last step is repeated four more times to give a residue which is taken up in 100 ml of methylene chloride and cooled to 0° C.; whereupon 0.9 ml of acetyl chloride and 1 ml of pyridine are added dropwise. After stirring 1 hour at 0° C., the resulting solution is washed with 3×50 ml of brine and dried over anhydrous magnesium sulfate. The solvent is removed and the residue is chromatographed to give trans-3-[o-nitrobenzyloxycarbonylamino]-4-[2-acetoxyethyl]-2-azetidinone (1.85 g).

i.r., μ; 3 (NH); 5.63 (β-lactam); 5.74 (carbamate ester).
nmr; (D$_6$-Acetone/D$_6$-DMSO) 7.5–8.27 (aromatic) 5.5s (benzylic CH$_2$); 4.4 dd (J=2; H=8; C3-H; trans); 4.15t (CH$_2$OAc); 2.00 S (CH$_3$).

Step B

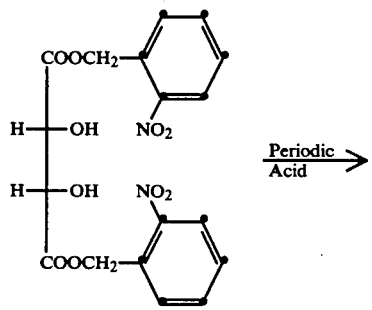

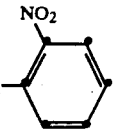

Periodic acid (2.28 g) is dissolved in 75 ml of tetrahydrofuran (THF) and 4.2 g of di-(o-nitrobenzyl)tartrate is added slowly. After stirring 1 hr. at 25° C., the mixture is diluted with 75 ml of benzene and the solids are filtered. The filtrate is concentrated in vacuo at 25° C. The residue, o-nitrobenzylglyoxylate, is used in the following Step C without further purification.

Step C

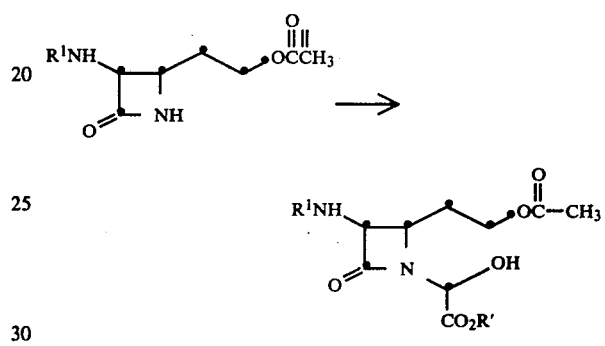

The o-nitrobenzylglyoxylate, from Step B, is dissolved in 100 ml of benzene and refluxed using a Dean-Stark water separator containing 5 g of CaH$_2$ for 0.5 hr; trans-3-[o-nitrobenzyloxycarbonylamino]-4-[2-acetoxyethyl]-2-azetidinone (3.51 g) is added and the mixture is refluxed for 6 hours, cooled and evaporated. The residue is chromatographed to give trans-1-(o-nitrobenzyloxycarbonylhydroxymethyl)-3-(o-nitrobenzyloxycarbonylamino)-4-(2-acetoxyethyl-2-azetidinone (3.8 g).

nmr: δ (D$_6$-Acetone) 7.0–8.3 (aromatic); 5.18 & 5.33 singlets (benzylic CH$_2$); 4.62 dd (J=2.5; J=8; C3-H; trans) 1.96 S (CH$_3$).
ir; (CDCl$_3$ soln) μ:5.61 (β-lactam); 5.73 (ester, carbamate).

Step D

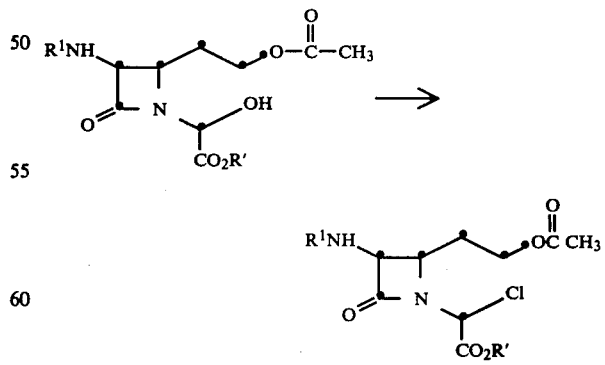

Trans-1-(o-nitrobenzyloxycarbonylhydroxymethyl)-3-(o-nitrobenzyloxycarbonylamino)-4-(2-acetoxyethyl)-2-azetidinone (560 mg) is dissolved in 25 ml of anhydrous THF and the solution is cooled to −30° C., under nitrogen; 100 μl of pyridine is added followed by 90 μl of thionylchloride. After stirring 0.5 hr. at −20°, the mixture is allowed to warm to 25° C. over 0.5 hr., and diluted with 25 ml of benzene. The solid is filtered and washed with 10 ml of benzene. The solvent from the filtrate is removed in vacuo at 25° C. The resulting residue, trans-1-(o-nitrobenzyloxycarbonylchloromethyl)-3-(o-nitrobenzyloxycarbonylamino)-4-(2-acetoxyethyl)-2-azetidinone, is used in the next reaction without further purification (yield: 520 mg).

Step E

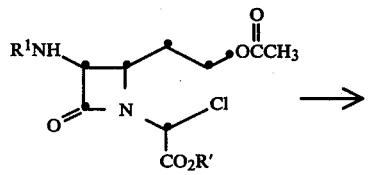

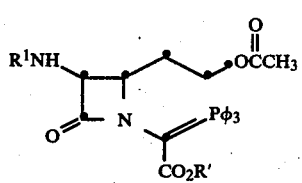

Trans-1-(o-nitrobenzyloxycarbonylchloromethyl)-3-(o-nitrobenzyloxycarbonylamino)-4-(2-acetoxyethyl)-2-azetidinone (520 mg) is dissolved in 5 ml of dry dimethylformamide (DMF) and 265 mg of triphenylphosphine is added. The resulting solution is kept overnight and the solvent is removed in vacuo at 35°–40° C. The residue is taken up in 30 ml of methylene chloride and washed with 20 ml of 0.5 N phosphate buffer (pH 7). The aqueous phase is washed with 10 ml of CH$_2$Cl$_2$. The combined CH$_2$Cl$_2$ extracts are dried over anhydrous MgSO$_4$ and the solvent is removed. The residue is chromatographed on silica gel to give trans-1-(benzyloxycarbonylmethylene triphenylphosphoranyl)-3-(o-nitrobenzyloxycarbonylamino)-4-(2-acetoxyethyl)-2-azetidinone (435 mg).

i.r., μ; 3.0 (NH); 5.65 shoulder (β-lactam); 5.73 (ester, carbamate); 6.1 (ylid ester).

Step F

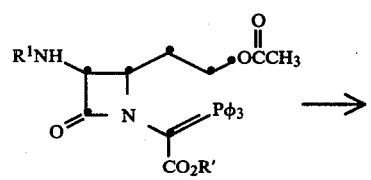

Trans-1-(o-nitrobenzyloxycarbonylmethylenetriphenylphosphoranyl)-3-(o-nitrobenzyloxycarbonylamino)-4-(2-acetoxyethyl)-2-azetidinone (161 mg) is dissolved in 2 ml of anhydrous methanol and 13 mg of sodium methoxide is added. The resulting mixture is stirred under nitrogen for 1 hour at 25° C. The solvent is removed in vacuo at 25° C. and the residue takes up in 25 ml of CH$_2$Cl$_2$ and washed with 2×20 ml of pH 7 phosphate buffer (0.5 N). The organic phase is dried over anhydrous MgSO$_4$ and the solvent is removed to give 124 mg of trans-1-(o-nitrobenzyloxycarbonylmethylenetriphenylphosphoranyl)-3-(o-nitrobenzyloxycarbonylamino)-4-(2-hydroxyethyl)-2-azetidinone.

EXAMPLE 5

Preparation of 6-amino-1-carbapen-2-em-3-carboxylic acid

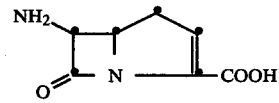

Step A

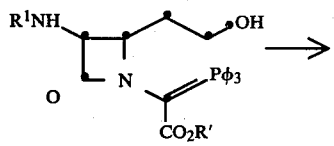

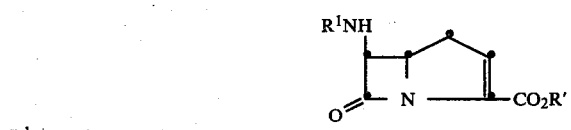

R$^1$ = o-nitrobenzyloxycarbonyl
R' = o-nitrobenzyl

Pyridinium chlorochromate (130 mg, 0.6 mmole) is suspended in 5 ml of anhydrous methylene chloride and 76 mg (0.1 mmole) of trans-1-(o-nitrobenzyloxycarbonylmethylenetriphenylphosphoranyl)-3-(o-nitrobenzyloxycarbonylamino)-4-(2-hydroxymethyl)-2-azetidinone in 5 ml of methylene chloride is added dropwise under nitrogen. After stirring 1 hour, the mixture is diluted with 10 ml of ether and the solid is filtered. The filtrate is washed with 10 ml of pH 3 phosphate buffer, followed by 10 ml of pH 7 phosphate buffer. The organic layer is dried and concentrated at 25° C. The residue is purified by preparative TLC to give 2 mg of the desired bicyclic material:

o-nitrobenzyl-1-carba-2-penem-6-α-o-nitrobenzyloxycarbonylamino)-3-carboxylate; i.r. μ (DMSO); 5.61 (β-lactam); 5.82 (ester and carbamate); 6.19 (double bond).

Step B

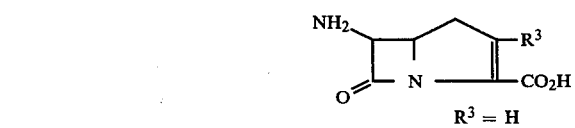

R$^3$ = H

A quantity (2 mg) of o-nitrobenzyl-1-carba-2-penem-6α(o-nitrobenzyloxycarbonylamino)-3-carboxylate is dissolved in 1.0 ml dioxane and 1.0 ml water and photolyzed under N$_2$ using 350 nm light in a Rayonet photolyser for 1.0 hr. at 25° C. The resulting reaction mixture is extracted with ethylacetate (3×2 ml) and then freeze dried to provide 1-carba-2-penem-6α-amino-3-carboxylic acid.

EXAMPLE 6

Preparation of Sodium 6-phenylacetamido-1-carbapen-2-em-3-carboxylate

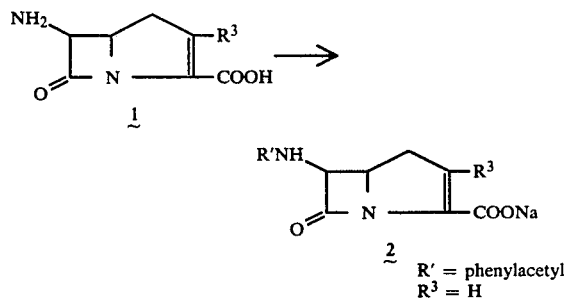

R' = phenylacetyl
R³ = H

To the 6-amino species (1) (1.68 mg, 0.1 mmole) in 2.0 ml. of 1:1 water/acetone, 2 equivalents of sodium bicarbonate is added. The mixture is cooled to 5° C. and 1 equivalent of acylhalide (phenylacetylchloride) is added. After stirring 1 hour, the solution is lyophilized to provide 2.

EXAMPLE 7

Sodium 6-phenylacetamido-1-carba-2-methyl-2-penem-3-carboxylate acid

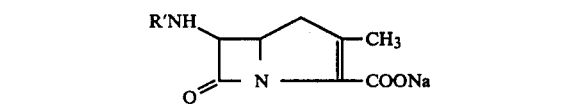

Step A 3-(o-nitrobenzyloxycarbonylamino)-1-(o-nitrobenzyloxycarbonylmethyltriphenyl-phosphoranyl)-4-(carboxymethyl)-2-azetidinone

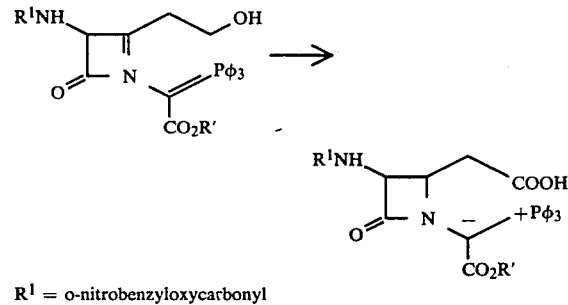

R¹ = o-nitrobenzyloxycarbonyl
R' = o-nitrobenzyl

One gram of 3-(o-nitrobenzyloxycarbonylamino)-1-(o-nitrobenzyloxycarbonylmethyltriphenylphosphoranyl)-4-(2-hydroxyethyl)-2-azetidinone is dissolved in 20 ml. acetone and cooled to 0° C. Jones Reagent (1 ml., 4 N solution) is added dropwise over 5 min. and the resulting solution is stirred at 0° C. for 10 min. Isopropanol (0.1 ml.) is added. The mixture is stirred for another 2 min. The reaction mixture is diluted with $CH_2Cl_2$ and filtered. The filtrate is washed with saturated NaCl solutin, dried and evaporated to give the title compound which is used without further purification in the next step.

Step B 3-(o-nitrobenzyloxycarbonylamino)-1-(o-nitrobenzyloxycarbonylmethyltriphenylphosphoranyl)-4-(chlorocarbonylmethyl)-2-azetidonone

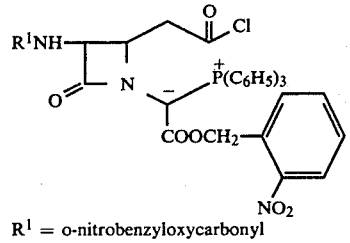

R¹ = o-nitrobenzyloxycarbonyl

The product of Step A (0.851 g.) is dissolved in 20 ml. $CH_2Cl_2$ and cooled to 0° C. under $N_2$. Oxalyl chloride (0.8 ml.) is added dropwise over 5 min. and then 1 drop of DMF is added. The mixture is stirred at 0° C. for 5 min. and then at 25° C. for 15 min. The solvent and excess oxalyl chloride are evaporated under reduced pressure. The residue is the desired acid chloride which is used without purification in the next step.

Step C 3-(o-nitrobenzyloxycarbonylamino)-1-(o-nitrobenzyloxycarbonyltriphenylphosphoranylmethyl)-4-(phenylthiocarbonylmethyl)-2-azetidinone

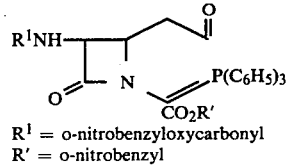

R¹ = o-nitrobenzyloxycarbonyl
R' = o-nitrobenzyl

The product from Step B is dissolved in 20 ml. $CH_2Cl_2$ and cooled to 0°, under $N_2$. Thiophenol (0.4 g.) is added and then pyridine (0.8 ml.) is added dropwise. The reaction mixture is stirred at 0° for 5 min. then at 25° C. for 15 min., then diluted with $CH_2Cl_2$ and washed with water, dried and evaporated. The residue is chromatographed on silica gel using 50% EtOAc/$C_6H_5$ as eluant to give the thio ester.

Step D 3-(o-nitrobenzyloxycarbonylamino)-1-(o-nitrobenzyloxycarbonyltriphenylphosphoranyl-methyl)-4-(methylcarbonylmethyl)-2-azetidinone

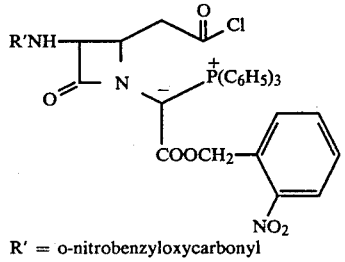

R' = o-nitrobenzyloxycarbonyl

Cuprous iodide (0.380 g.) is suspended in 10 ml. anhydrous ether under $N_2$, in a dry flask and cooled to 0° C. Methyl lithium (3.0 ml., 1.3 Molar) is added dropwise and the mixture is stirred at 0° for 5 min. to give a yellow suspension. The mixture is then cooled to −50°. The product of Step C (0.674 g.) in 10 ml. THF is added dropwise over 5 min. The mixture is stirred at −50° for 5 min. and allowed to come to −20° over 20 min. and stirred at −20° for 5 min. Saturated NH₄Cl solution 5 ml. is added; the mixture is diluted with CH₂CL₂; and stirred at 25° C. for 5 min. The organic phase is separated, dried and evaporated. The residue is chromatographed on silica gel using EtOAc as eluant to give the title compound.

Step E o-Nitrobenzyl-6-(o-nitrobenzyloxycarbonylamino)-1-carba-2-methyl-2-penem-3-carboxylate

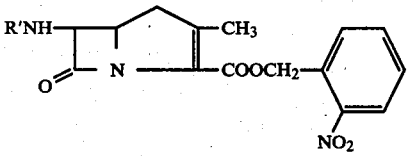

In xylene (3 ml.), the product of Step D (0.030 g.) is dissolved, pyridine (0.010 ml.) is added and the mixture is heated under N₂ at 140° for 40 min. The xylene is removed under reduced pressure and the residue is purified by preparatory thin layer chromatography on silica gel using 50% EtOAc/C₆H₆ as eluant to give the title compound.

Step F

Sodium-1-carba-2-methyl-2-penem-3-carboxylate

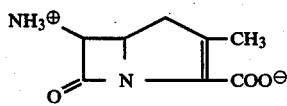

The product of Step E, (0.10 g.) is dissolved in dioxane (2 ml.) and water (2 ml.) pH 7 phosphate buffer (0.1 ml, (0.5 Molar) is added and the mixture is deoxygenated by bubbling N₂ through the mixture. The mixture is photolysed for 1 hr. using 350 nm light in a pyrex vessel cooled by a cold finger. The photolysis mixture is extracted with ethyl acetate. The aqueous phase is freeze dried to give the title compound.

Step G

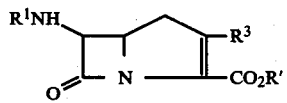

R' = Na
R¹ = phenylacetyl
R³ = methyl

Following the procedure of Example 6, except making the indicated substitution, the title compound is obtained.

EXAMPLE 8

Sodium-6-phenylacetamido-1-carba-2-phenyl-2-penem-3-carboxylate

Step A 3-(o-nitrobenzyloxycarbonylamino)-1-(o-nitrobenzyloxycarbonyltriphenylphosphoranylmethyl)-4-(phenylcarbonylmethyl)-2-azetidinone

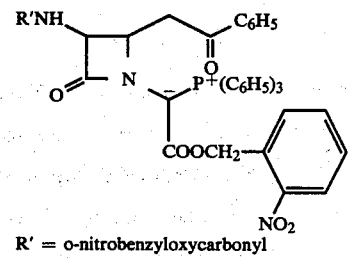

R' = o-nitrobenzyloxycarbonyl

Following the procedure described in Example 7, Step D, but substituting an equivalent amount of phenyl lithium (or phenyl magnesium bromide) for methyl lithium, there is obtained the title compound.

Step B o-nitrobenzyl-6-(o-nitrobenzyloxycarbonylamino)-1-carba-2-phenyl-3-carboxylate

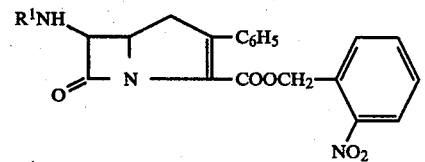

R¹ = o-nitrobenzyloxycarbonyl

The product of Step A, (0.030 g), is dissolved in xylene (3 ml) and heated under N₂ at 140° for 40 min. The xylene is removed under reduced pressure and the residue purified by preparatory tlc on silica gel to give the title compound.

Step C

6-Amino-1-carba-2-phenyl-2-penem-3-carboxylic acid

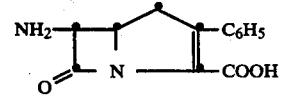

A quantity of (5 mg) o-nitrobenzyl-6-(o-nitrobenzyloxycarbonylamino)-1-carba-2-phenyl-2-penem-3-carboxylate is dissolved in 1 ml dioxane, 1 ml water and 0.1 ml ethanol; 5 mg of Pd/C are added and the mixture is hydrogenated at 40 psi H₂ for 0.5 hr. The catalyst is filtered off and the filtrate is extracted with ether and the aqueous phase is freeze dried to give the title compound.

Step D

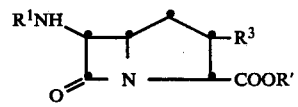

R¹ = phenylacetyl
R³ = phenyl
R' = Na⁺

Following the procedure of Example 6, except making the indicated substitution, the title compound is obtained.

EXAMPLE 9

Following the procedure developed in the foregoing Examples and text, the following compounds of the present invention, I, are obtained and displayed in Table I. Remarks relative to the procedures are presented in the footnote to Table I. (In the table, $\phi$=phenyl).

TABLE I $$R^1NH \begin{array}{c} \\ \diagdown \\ O \end{array} \begin{array}{c} \bullet \\ N \end{array} \begin{array}{c} R^3 \\ \diagup \\ CO_2R' \end{array} \quad I$$

| Compound | $R^1$ | $R^3$ | $R'$ |
|---|---|---|---|
| (1.) | $\phi CH_2C(O)-$ | H | Na |
| (2.) | $\phi CH_2C(O)-$ | $\phi$ | Na |
| (3.) | $\phi CH_2C(O)-$ | $CH_3$ | Na |
| (4.) | $\phi CH_2C(O)-$ | $\overset{H}{\underset{CH_3\ \ CH_3}{\diagup\!\diagdown}}$ | Na |
| (5.) | $\phi CH_2C(O)-$ | para-$\phi CH_2NH_2$ | H |
| (6.) | $\phi CH_2C(O)-$ | para-$\phi CH_2OH$ | Na |
| (7.) | $\phi CH(NH_2)C(O)-$ | para-$\phi OCH_3$ | H |
| (8.) | $\phi CH(NH_2)C(O)-$ | $\overset{H}{\underset{CH_3\ \ CH_3}{\diagup\!\diagdown}}$ | H |
| (9.) | thienyl-CH(CO$_2$Na)-C(O)- | $\phi$-CH$_2$NH$_2$ (para-$\phi CH_2NH_2$) | H |
| (10.) | $\phi CH(CO_2Na)C(O)-$ | $\phi$ | Na |
| (11.) | $\phi CH(OH)C(O)-$ | para-$\phi CH_2NH_2$ | H |
| (12.) | isothiazolyl-CH$_2$C(O)- | para-$\phi CH_2NH_2$ | H |

FOOTNOTES TO TABLE I
(1.) As in Example 6.
(2.) As in Example 8. $\neq$(3.) As in Example 7.

(4.) As described in Example 7, but sustituted MgBr in place of CH$_3$Li in Step D.
$\left[ \overset{H}{\underset{CH_3\ \ CH_3}{\diagup\!\diagdown}} \right]$ (5.) Start with product of Step B, Example 3. Acylate with $\phi CH_2COCL$ rather than o-nitrobenzyloxycarbonyl chloride and 7 butarry the amide produced through Steps of Examples substitute ($\phi$—CH$_2$OTHP)MgBr for CH$_3$Li in Step D of Example 7. Follow by acid hydrolysis of the THP ether in the product; convert the alcohol produced to the mesylate and displacement with sodium azide to give the azido methyl phenyl ketone which is cyclized as in Step E, followed by the procedure of Step C of Example 8.
(6.) Cyclization of the keto- alcohol in (5.) and deprotection and acylation using the procedure of Step C and D of Example 8.

(7.) As described in Example 7, but substituted ($\phi$—OCH$_3$)

MgBr for CH$_3$Li in Step D; use $\phi$CHCOCl as acylating agent in Step G. | NH$_3$CL (8.) As for (7.) except ( CH$_3$—CH=CH—CH$_3$ ) MgBr is used in Step D rather than CH$_3$Li.

(9.) As for (5.) except that thienyl-CHCOCl (R= o-nitrobenzyl) | CO$_2$R
is used instead of $\phi CH_2COCL$.

(10.) As for (2.) except that $\phi$—CH(COCL)—COCL is used instead of the $\phi CH_2COCl$ of Step D of Example 8.

(11.) As for (5.) except $\phi$—CHCOCl (R= o-nitrobenzyl) is used | O—C(=O)—OR
instead of $\phi CH_2COCL$.

(12.) As for (5.) except that isothiazolyl-CH$_2$COCl is used instead (2.) of $\phi CH_2COCl$.

EXAMPLE 10

Preparation of Pharmaceutical Compositions

One such unit dosage form consists in mixing 120 mg. of 6-phenylacetamido-1-carba-2-phenyl-pen-2-em-3-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 6-phenylacetamido-1-carba-2-phenyl-pen-2-em-3-carboxylic acid | 125 mg. |
| Cornstarch, U.S.P. | 6 mg. |
| Dicalcium Phosphate | 192 mg. |
| Lactose, U.S.P. | 190 mg. |
| Magnesium stearate | balance |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | |
| 6-phenylacetamidol-1-carba-2-phenyl-pen-2-em-3-carboxylic acid | | 500 mg. |
| Sterile Water | | 2 ml. |
| OPTHALMIC SOLUTION | | |
| 6-phenylacetamido-1-carba-2-phenyl-pen-2-em-3-carboxylic acid | | 100 mg. |
| Hydroxypropylmethyl cellulose | | 5 mg. |
| Sterile Water | to | 1 ml. |
| OTIC SOLUTION | | |
| 6-phenylacetamido-1-carba-2-phenyl-pen-2-em-3-carboxylic acid | | 100 mg. |
| Benzalkonium Chloride | | 0.1 mg. |
| Sterile Water | to | 1 ml. |
| TOPICAL OINTMENT | | |
| 6-phenylacetamido-1-carba-2-phenyl-pen-2-em-3-carboxylic acid | | 100 mg. |
| Polyethylene Glycol 4000 U.S.P. | | 400 mg. |
| Polyethylene Glycol 400 U.S.P. | | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the following structural formula:

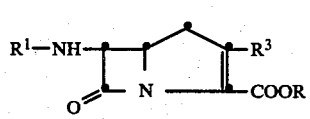

wherein

R is a pharmaceutically acceptable salt or benzyl, p-nitrobenzyl, o-nitrobenzyl, t-butyl, bromo-t-butyl, t-butyl-dimethylsilyl, trimethylsilyl, trichloroethyl;

$R^1$ is phenylacetyl, D-phenylglycyl, ($\alpha$-carboxy)-2-thienylacetyl, ($\alpha$-carboxy)phenylacetyl, $\alpha$-hydroxyphenylacetyl, or 3-isothiazoylacetyl;

and $R^3$ is substituted and unsubstituted: loweralkyl having from 1 to 4 carbon atoms, lower alkenyl having 2-6 carbon atoms, or phenyl wherein the substituent is selected from the group consisting of hydroxyl, amino, amidino, guanidino, phenyl, aminoalkyl, hydroxyalkyl, mercapto, carboxyl, trifluoromethyl, loweralkylthio, and loweralkoxyl wherein the alkyl or alkoxyl has 1 to 6 carbon atoms.

2. The compound of claim 1 wherein $R^3$ is H, $C_6H_5$, $CH_3$,

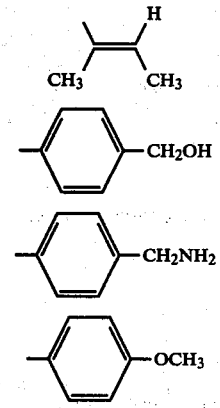

3. A compound according to claim 2 wherein $R^1$ is

and $R^3$ is H.

4. A compound according to claim 2 wherein $R^2$ is

and $R^3$ is $C_6H_5$.

5. A compound according to claim 2 wherein $R^1$ is

and $R^3$ is $CH_3$.

6. A compound according to claim 2 wherein

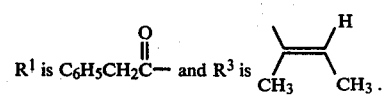

7. A compound according to claim 2 wherein

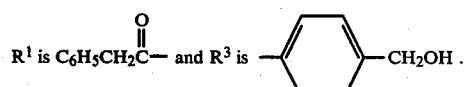

8. A compound according to claim 2 wherein

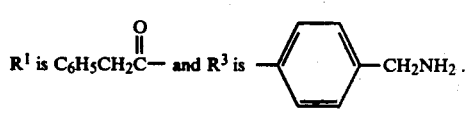

9. A compound according to claim 2 wherein

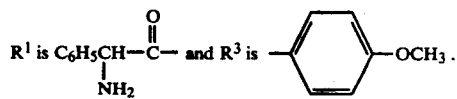

10. A compound according to claim 2 wherein

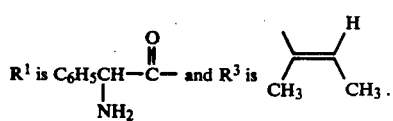

11. A compound according to claim 2 wherein

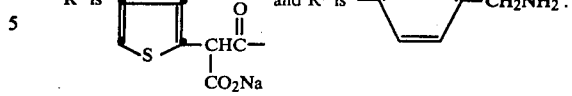

12. A compound according to claim 2 wherein

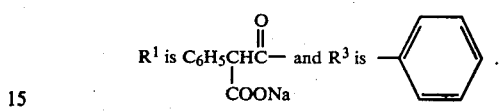

13. A compound according to claim 2 wherein

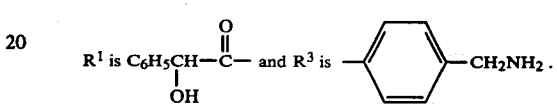

14. A compound according to claim 2 wherein

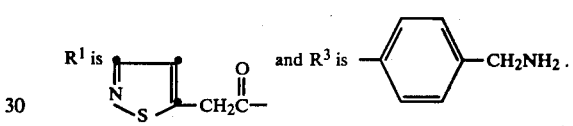

15. A pharmaceutical antibiotic compositions comprising, in unitary dosage form, a therapeutically effective amount of a compound according to claim 2 and a pharmaceutical carrier therefor.

* * * * *